(12) United States Patent
Peiffer et al.

(10) Patent No.: US 7,708,151 B2
(45) Date of Patent: May 4, 2010

(54) MEMBRANE FOR SEPARATING AROMATIC AND ALIPHATIC COMPOUNDS

(75) Inventors: Dennis G. Peiffer, Annandale, NJ (US); Randall D. Partridge, Califon, NJ (US); Walter Weissman, Basking Ridge, NJ (US); David C. Dalrymple, Bloomsbury, NJ (US); Craig Y. Sabottke, Annandale, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 438 days.

(21) Appl. No.: 11/890,226

(22) Filed: Aug. 3, 2007

(65) Prior Publication Data

US 2008/0035573 A1 Feb. 14, 2008

Related U.S. Application Data

(60) Provisional application No. 60/836,320, filed on Aug. 8, 2006.

(51) Int. Cl.
*B01D 71/64* (2006.01)
*B01D 61/00* (2006.01)

(52) U.S. Cl. .............. 210/500.39; 210/500.1; 210/500.27; 210/652; 210/653; 528/274; 528/290

(58) Field of Classification Search .............. None
See application file for complete search history.

(56) References Cited

U.S. PATENT DOCUMENTS

| | | | |
|---|---|---|---|
| 4,650,574 A | 3/1987 | Hilgendorff et al. | |
| 4,914,064 A | 4/1990 | Schucker | |
| 4,929,358 A | 5/1990 | Koenitzer | |
| 4,944,880 A | 7/1990 | Ho et al. | |
| 4,946,594 A | 8/1990 | Thaler et al. | |
| 4,962,270 A | 10/1990 | Feimer et al. | |
| 4,990,275 A | 2/1991 | Ho et al. | |
| 5,130,017 A | 7/1992 | Schucker | |
| 5,138,023 A | 8/1992 | Sartori et al. | |
| 5,230,801 A * | 7/1993 | Darnell et al. | 210/640 |
| 5,275,726 A | 1/1994 | Feimer et al. | |
| 5,445,731 A | 8/1995 | Tuohey et al. | |
| 5,550,199 A | 8/1996 | Ho et al. | |
| 5,635,055 A | 6/1997 | Sweet et al. | |
| 5,670,052 A | 9/1997 | Ho et al. | |
| 5,685,990 A | 11/1997 | Saugmann et al. | |
| 5,756,643 A | 5/1998 | Ho et al. | |
| 5,855,647 A | 1/1999 | Li et al. | |
| 6,096,114 A | 8/2000 | Li et al. | |
| 6,203,713 B1 | 3/2001 | Tanny | |

(Continued)

FOREIGN PATENT DOCUMENTS

WO  WO 2006/040307 A1  4/2006

(Continued)

*Primary Examiner*—Krishnan S Menon
(74) *Attorney, Agent, or Firm*—D. M. Weisberg

(57) ABSTRACT

This invention relates to a polymeric membrane composition utilizing the non-hazardous compound 4-aminophenyl disulfide ("APD"), a method of making the polymeric membrane, and a process for separating components of a feedstream utilizing the polymeric membrane. More particularly, but not by way of limitation, this invention relates to utilizing the polymeric membrane composition in a process for the separation of aromatics from a hydrocarbon feedstream containing aromatics and aliphatic compounds.

21 Claims, 3 Drawing Sheets

U.S. PATENT DOCUMENTS

| | | |
|---|---|---|
| 6,645,383 B1 | 11/2003 | Lee et al. |
| 2003/0150795 A1* | 8/2003 | Dorgan et al. .......... 210/500.21 |
| 2004/0000513 A1 | 1/2004 | Colling et al. |
| 2004/0004040 A1 | 1/2004 | Colling et al. |
| 2006/0081500 A1 | 4/2006 | Bitterlich et al. |
| 2007/0095756 A1* | 5/2007 | Hardwicke et al. .......... 210/652 |

FOREIGN PATENT DOCUMENTS

WO    WO 2006/066269 A2    6/2006

* cited by examiner

MEMBRANE FOR SEPARATING AROMATIC AND ALIPHATIC COMPOUNDS

CROSS-REFERENCE TO RELATED APPLICATIONS

This application is a United States utility application which claims priority to U.S. Provisional Patent Application Ser. No. 60/836,320, filed Aug. 8, 2006.

FIELD OF THE INVENTION

This invention relates to a polymeric membrane composition utilizing the non-hazardous compound 4-aminophenyl disulfide ("APD"), a method of making the polymeric membrane, and a process for separating components of a feedstream utilizing the polymeric membrane. More particularly, but not by way of limitation, this invention relates to utilizing the polymeric membrane composition in a process for the separation of aromatics from a hydrocarbon feedstream containing aromatics and aliphatic compounds.

BACKGROUND OF THE INVENTION

Polymeric membrane based separation processes such as reverse osmosis, pervaporation and perstraction are conventional. In the pervaporation process, a desired feed component, e.g., an aromatic component, of a mixed liquid feed is preferentially absorbed by the membrane. The membrane is exposed at one side to a stream comprised of a mixture of liquid feeds and a vacuum is applied to the membrane at the opposite side so that the absorbed component migrates through the membrane and is removed as a vapor from the opposite side of the membrane via a solution-diffusion mechanism. A concentration gradient driving force is therefore established to selectively pass the desired components through the membrane from its upstream side to its downstream side.

The perstraction process is utilized to separate a liquid stream into separate products. In this process, the driving mechanism for the separation of the stream into separate products is provided by a concentration gradient exerted across the membrane. Certain components of the fluid will preferentially migrate across the membrane because of the physical and compositional properties of both the membrane and the process fluid, and will be collected on the other side of the membrane as a permeate. Other components of the process fluid will not preferentially migrate across the membrane and will be swept away from the membrane area as a retentate stream. Due to the pressure mechanism of the perstraction separation, it is not necessary that the permeate be extracted in the vapor phase. Therefore, no vacuum is required on the downstream (permeate) side of the membrane and permeate emerges from the downstream side of the membrane in the liquid phase. Typically, permeate is carried away from the membrane via a swept liquid.

The economic basis for performing such separations is that the two products achieved through this separation process (i.e., retentate and permeate) have a refined value greater than the value of the unseparated feedstream. Membrane technology based separations can provide a cost effective processing alternative for performing the product separation of such feedstreams. Conventional separation processes such as distillation and solvent extraction can be costly to install and operate in comparison with membrane process alternatives. These conventional based processes can require a significant amount of engineering, hardware and construction costs to install and also may require high levels of operational and maintenance personnel costs to maintain the associated facilities in an operating status. Additionally, most of these processes require the heating of the process streams to relatively high temperatures in order to separate different components during the processing steps resulting in higher energy costs than are generally required by low-energy membrane separation processes.

In general, the membrane technology in the present art has the benefit of lower per unit energy costs per volume of separation than the conventional technologies in present art. However, a major obstacle in perfecting the commercial operation of membrane separation technologies is to improve the flux and selectivity characteristics of the current membrane systems in order to make the construction costs and separation efficiencies of membrane technologies economically viable, for example, on a refinery scale operations and on-board vehicle separation processes.

A myriad of polymeric membrane compositions have been developed over the years. Such compositions include polyurea/urethane membranes (U.S. Pat. No. 4,914,064); polyurethane imide membranes (U.S. Pat. No. 4,929,358); polyester imide copolymer membranes (U.S. Pat. No. 4,946,594); polyimide aliphatic polyester copolymer membranes (U.S. Pat. No. 4,990,275); and diepoxyoctane crosslinked/esterfied polyimide/polyadipate copolymer (diepoxyoctane PEI) membranes (U.S. Pat. No. 5,550,199).

These copolymeric membranes are generally comprised of "soft segments" and "hard segments" which form polymer chains in the membrane. The soft segments of the polymer provide the active area for the selective diffusion of the permeate through the membrane. However, these soft segments of the membrane have limited structural and thermal strength characteristics. Therefore, in order to provide structural strength to the membrane, a hard segment polymer (e.g., the reaction product of a dianhydride and a diamine) is added to the soft segment polymer in a suitable solvent to form long copolymer chains in the final membrane preferably comprised of alternating soft and hard polymer segments. These hard segments provide significant mechanical and thermal stability to the membrane, but are essentially non-permeable to the process stream components. These copolymer membranes of the prior art then undergo a high temperature "thermal cross-linking" to further promote molecular bonding between these copolymer chains in the final membrane composition.

For a given polymeric membrane composition, the flux across a given membrane is generally inversely proportional to the thickness of the membrane. Therefore, the cross-section of a constructed membrane is commonly very thin (on the order of about 0.1 to about 50 microns) in order to derive the selectivity benefit of the membrane while maximizing the flux characteristics of the membrane. However, for a membrane operated at constant feed composition and process conditions, the selectivity of a particular membrane composition is substantially independent of the thickness of the membrane and is principally dependent upon the compositional characteristics of the membrane.

Therefore, in order to increase the selectivity for membrane processes, new membrane compositions must be discovered that have improved selectivity characteristics. Although a high flux capacity of a membrane is desired, deficiencies in a membrane composition's flux characteristics can be overcome by increasing the active membrane area or fabricating membranes of thinner cross sections. Similar "mechanical variables" generally cannot be utilized to improve a membrane composition's inherent selectivity performance.

Additionally, some of the compounds that are utilized in the present art for the fabrication of polymeric membranes are categorized as toxic to human life and/or harmful to the environment. In particular, two of these compounds of concern, methylene dianiline ("MDA") and methylene diochloroaniline ("MOCA"), are used in the fabrication of the polyethylene adipate (PEA)/diepoxy based membranes in the prior art (see U.S. Pat. Nos. 4,990,275 and 5,550,199 to Ho et al.). The Sigma-Aldrich chemical company website classifies MDA as toxic, a possible carcinogen, and harmful to aquatic environments. Sigma-Aldrich, Chemical Name 4,4'-Methylene-$^{13}$C-dianiline <http://www.sigmaaldrich.com/catalog/search/ProductDetail/ALDRICH/491500> (accessed May 8, 2006). The Sigma-Aldrich chemical company website classifies MOCA as toxic, a possible carcinogen, and extremely harmful to aquatic environments. Sigma-Aldrich, Chemical Name 4,4'-Methylene-bis(2-chloroaniline), <http://www.sigmaaldrich.com/catalog/search/ProductDetail/ALDRICH/117323>, (accessed May 8, 2006).

The use of hazardous components in the fabrication of polymeric membranes also results in higher costs of manufacturing due to increased shipping and handling costs as well as higher costs for the installation, operation and maintenance of personnel and environmental protective equipment required for the manufacture and handling of these compounds. Therefore, in addition to the potential health concerns and potential adverse environment aspects of utilizing hazardous components, there is also is an economically driven need in the industry associated with the discovery and utilization of new non-hazardous materials for the fabrication of membranes which can meet or exceed the processing capabilities, durability and performance of the polymeric membranes of the prior art.

Therefore there is a need in the industry for new membrane compositions with improved inherent selectivity characteristics. There is also a separate need in the industry for new membrane compositions utilizing materials which possess non-toxic and minimal negative environmental impact properties.

SUMMARY OF THE INVENTION

The present invention relates to a polymeric membrane composition utilizing the non-hazardous compound 4-aminophenyl disulfide (APD), a method of making the polymeric membrane, and a process for separating components of a feedstream utilizing the polymeric membrane. In particular, the polymeric membrane is utilized in a process for selectively separating aromatics from a hydrocarbon feedstream comprised of aromatic and aliphatic hydrocarbons.

In one embodiment, the present invention relates to the composition of a polymeric membrane effective in selectively separating components of a hydrocarbon feedstream. In particular, the present invention relates to the composition of a polymeric membrane effective in the selective separation of aromatics from a hydrocarbon stream containing both aromatics and non-aromatics. This invention results in a membrane composition with improved separation characteristics over the prior art. Another important aspect is that this new polymeric membrane composition utilizes a non-hazardous component that eliminates the need for hazardous polymer chain-extension compounds utilized in the prior art.

In an embodiment, the present invention relates to a copolymer composition of matter comprised of a polyimide hard segment and a soft segment containing an aliphatic polyester wherein said polyimide hard segment is comprised of pyromellitic dianhydride (PMDA) and 4-aminophenyl disulfide (APD).

In a preferred embodiment, the soft segment of the membrane composition is comprised of one or more compounds selected from the group consisting of a polyadipate, a polysuccinate, a polymalonate, a polyoxalate, and a polyglutarate.

In another preferred embodiment, the membrane composition is comprised of a polyimide hard segment and a soft segment that are chemically cross-linked with improved glass transition temperatures ($T_g$) of the hard and soft segments of the resultant membranes. In a preferred embodiment of the present invention, the membrane has a soft segment $T_g$ of less than 77° F. (25° C.), preferably less than 32° F. (0° C.), more preferably less than −13° F. (−25° C.). In another embodiment, the membrane also has a hard segment $T_g$ of greater than 212° F. (100° C.), preferably greater than 248° F. (120° C.). All glass transition temperatures referenced herein are based on measurements taken from a solvent-free membrane after fabrication and prior to exposure to any external feed or pre-treatment media (i.e., in the "unswollen" condition).

In a more preferred embodiment, the membrane composition of the present invention is comprised of a polyethylene adipate (PEA), pyromellitic dianhydride (PMDA), 4-aminophenyl disulfide (APD), and a chemically cross-linking agent.

In another more preferred embodiment, the polyethylene adipate (PEA) is present in a molar range of about 0.25 to about 2.0, the pyromellitic dianhydride (PMDA) is present in a molar range of about 0.5 to about 4.0, the 4-aminophenyl disulfide (APD) is present in a molar range of about 0.25 to about 2.0, and the chemically cross-linking agent is present in a molar range of about 0.5 to about 4.0. More preferably, the polyethylene adipate (PEA) is present in a molar range of about 0.5 to about 1.5, the pyromellitic dianhydride (PMDA) is present in a molar range of about 1.0 to about 3.0, the 4-aminophenyl disulfide (APD) is present in a molar range of about 0.5 to about 1.5, and the chemically cross-linking agent is present in a molar range of about 1.0 to about 3.0. Even more preferably, the polyethylene adipate (PEA), the pyromellitic dianhydride (PMDA), the 4-aminophenyl disulfide (APD), and chemically cross-linking agent are present in molar amounts of substantially 1, 2, 1, and 2, respectively.

In still another more preferred embodiment, the final copolymer membrane solution is cured at temperatures from about 212° F. to about 482° F. (100° C. to about 250° C.), preferably from about 212° F. to about 392° F. (100° C. to about 200° C.) which allows the endothermic chemical cross-linking reactions to take place during the curing and formation of the final membrane.

In another embodiment, the membranes of the present invention are utilized in a process for separating aromatics from a hydrocarbon feedstream comprised of aromatic and non-aromatics by selectively permeating the aromatics through the membrane.

In still a more preferred embodiment, said hydrocarbon feedstream is a naphtha with a boiling range of about 50° F. (10° C.) to about 450° F. (232° C.), and contains aromatic and non-aromatic hydrocarbons.

In another embodiment, said hydrocarbon feedstream is comprised of aromatics, non-aromatics, sulfur heteroatoms, and nitrogen heteroatoms, and said sulfur and nitrogen heteroatoms are selectively permeated through said polymeric membrane.

DETAILED DESCRIPTION OF THE PREFERRED EMBODIMENTS

Figure 1:
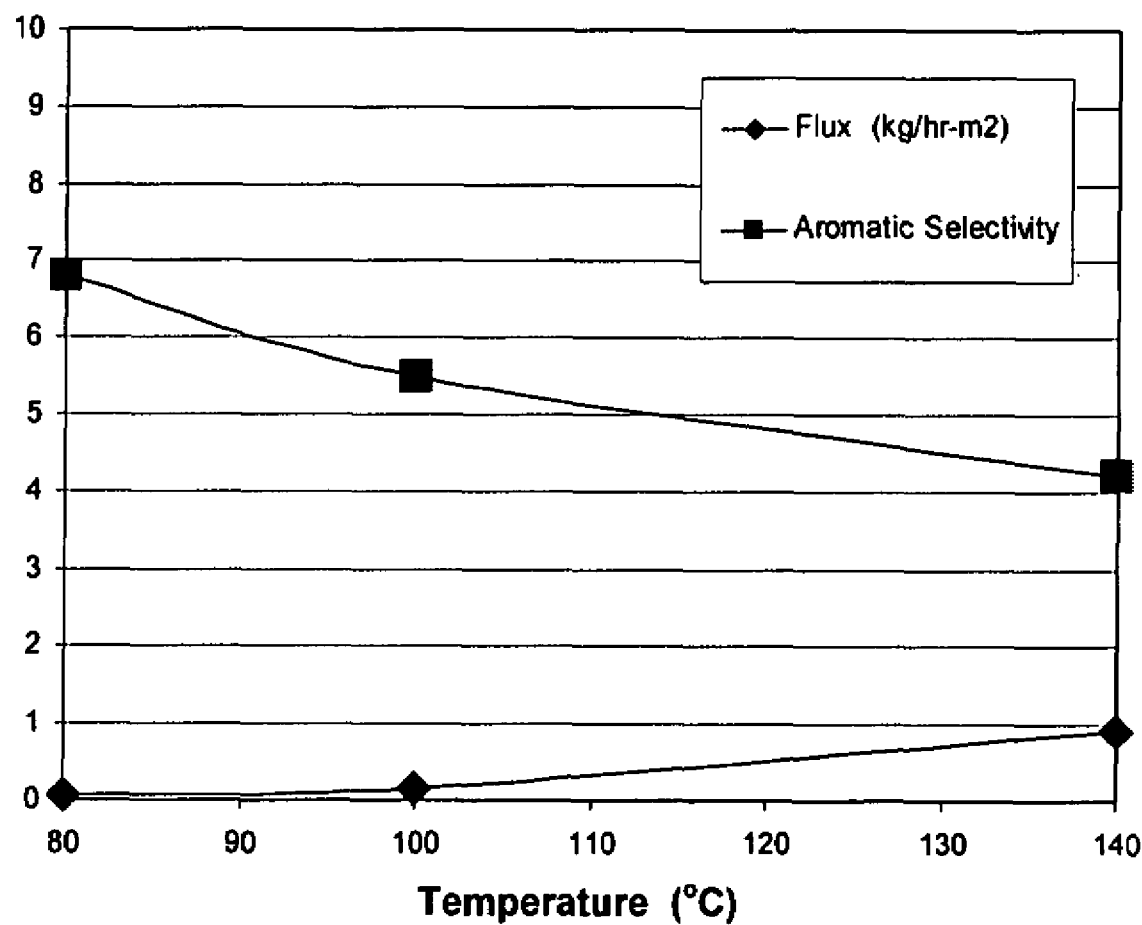
FIG. 1 shows the flux and selectivity of a membrane assembly composed of one embodiment of the membranes of the present invention subjected to a model gasoline feed under pervaporation conditions.

As used herein, the term "hydrocarbon" means an organic compound having a predominantly hydrocarbon character. Accordingly, organic compounds containing one or more non-hydrocarbon radicals (e.g., sulfur or oxygen) would be within the scope of this definition. As used herein, the terms "aromatic hydrocarbon" or "aromatic" means a hydrocarbon-based organic compound containing at least one aromatic ring. The rings may be fused, bridged, or a combination of fused and bridged. In a preferred embodiment, the aromatic species separated from the hydrocarbon feed contains one or two aromatic rings. The terms "non-aromatic hydrocarbon" or "non-aromatic" or "saturate" means a hydrocarbon-based organic compound having no aromatic cores. Also as used herein, the terms "thermally cross-linked" or "thermal cross-linking" means a membrane curing process at curing temperatures typically above about 250 to 300° C. (482 to 572° F.) characterized by the random formation of secondary interactions (e.g., hydrogen bonding, dipolar bonding, and the like) and chemical bonding of neighboring polymeric chains in solution. The term "chemically cross-linked" or "chemical cross-linking" means a chemical curing process characterized by the principal reaction of chemical bonding of neighboring polymeric chains via selected incorporation of structurally-defined chemical crosslinkers thereby forming a three-dimensional polymer network. Also as used herein, the term "selectivity" means the ratio of the desired component (s) in the permeate to the non-desired component(s) in the permeate divided by the ratio of the desired component(s) in the feedstream to the non-desired component(s) in the feedstream. Also, the term "flux" or "normalized flux" is defined the mass rate of flow of the permeate across a membrane usually in dimensions of $Kg/m^2$-day, $Kg/m^2$-hr, $Kg$-$\mu m/m^2$-day, or $Kg$-$\mu m/m^2$-hr. Also used herein, the term "selective" means that the described part has a tendency to allow one or more specific components of the feedstream to preferentially pass through that part with respect to the other feedstream components. The terms "non-aromatics" and "aliphatics" are used interchangeably in this document.

The present invention involves the composition of polymeric membranes useful in processes for separating components of a feedstream, in particular, the polymeric membranes of the present invention are useful in the selective separation of aromatics from a hydrocarbon stream comprised of both aromatics and non-aromatics.

The present invention consists of polymeric membrane compositions utilizing 4-aminophenyl disulfide ("APD") as a chain extender in the polymer hard segment and the use of these membranes in a process for separating components of a feedstream, in particular, the polymeric membranes of the present invention are useful in the selective separation of aromatics from a hydrocarbon stream comprised of both aromatics and non-aromatics. In a particular embodiment, the present invention utilizes a very low final curing temperature from about 212° F. to about 482° F. (100° C. to about 250° C.), preferably from about 212° F. to about 392° F. (100° C. to about 200° C.) in order to preserve the integrity of the membrane. In particular this low temperature cure preserves the structural composition of the soft segment portion of the membrane while allowing the endothermic cross-linking reactions to occur linking the copolymer hard segments. The use of APD as a chain extender and the use of this low final curing temperature improve the selectivity of the resultant membrane in processes for aromatics separation.

Another particular benefit of utilizing APD in the fabrication of these new polymeric membrane compositions is that the particularly hazardous chain extension components of the prior art, such as methylene dianiline ("MDA") and methylene diochloroaniline ("MOCA") may be eliminated. MDA and MOCA are classified as toxic to human life and/or harmful to the environment. The Sigma-Aldrich chemical company website classifies MDA as toxic, a possible carcinogen, and harmful to aquatic environments. Sigma-Aldrich, Chemical Name 4,4'-Methylene-$^{13}$C-dianiline <http://www.sigmaaldrich.com/catalog/search/ProductDetail/ALDRICH/491500> (accessed May 8, 2006). The Sigma-Aldrich chemical company website classifies MOCA as toxic, a possible carcinogen, and extremely harmful to aquatic environments. Sigma-Aldrich, Chemical Name 4,4'-Methylene-bis (2-chloroaniline) <http://www.sigmaaldrich.com/catalog/search/ProductDetail/ALDRICH/117323>, (accessed May 8, 2006).

In contrast, the 4-aminophenyl disulfide ("APD") utilized in the present invention is classified as non-toxic and not dangerous to the environment. The Sigma-Aldrich chemical company website classifies APD only as an irritant with minimal associated required safety precautions. Sigma-Aldrich, Chemical Name 4-Aminophenyl disulfide <http://www.sigmaaldrich.com/catalog/search/ProductDetail/ALDRICH/369462, (accessed May 8, 2006).

An embodiment of the copolymer membrane of the present invention was synthesized by reacting one mole of polyethylene adipate (PEA) with two moles of pyromellitic dianhydride (PMDA), to make a prepolymer in the end-capping step. This prepolymer was dissolved in a suitable solvent such as dimethylformamide (DMF). One mole of 4-aminophenyl disulfide (APD) was added to make a copolymer in the chain extension step. Additional DMF was added to the solution as well as acetone to prevent gelling and to provide for proper wettability of the solution on the substrate support. Subsequently, two moles of diepoxycyclooctane were added to the copolymer solution in the chemical cross-linking step. The new membrane was prepared by casting the solution onto a porous support (in this case, a 0.2 micron porous Gore-Tex® polytetrafluoroethylene fabric, a product of W. L. Gore and Associates), adjusting the thickness by means of a casting knife. The membrane then underwent a drying step in which most of the solvent was removed from the casting at room temperature in a box purged with nitrogen. The final casting was then subjected to a low temperature cure of 150° C. (302° F.) for 1.5 hours in order to promote a chemically cross-linking of the pendant carboxylic acid groups producing the resultant ester-alcohol functionalities. This low-temperature solvent drying/curing procedure is of significant importance in initiating the chemical cross-linking of the pendant hard segments in the membrane without thermal decomposition or oxidation of the PEA soft segment which would result from curing the membrane casting at higher temperatures above about 250 to 300° C. (482 to 572° F.).

The resulting membrane composition possesses improved selectivity properties. The present invention also eliminates the need for hazardous chain-extension compounds in membrane compositions of the prior art.

FIG. 1 shows the flux and selectivity at different temperatures of a membrane assembly composed of one embodiment of the membranes of the present invention subjected to a model gasoline feed under pervaporation conditions. The process data in the figure was obtained from subjecting a membrane assembly comprised two APD/PMDA hard segment membranes from Example 1, which were placed face-to-face (i.e., the porous casting supports faced outward in the stack) and the membrane assembly was subjected to the feed composition and pervaporation conditions further described in Example 3 below. As can be seen in FIG. 1, the membrane demonstrates a high aromatic selectivity ranging from a selectivity of greater than 4 at 140° C. (284° F.) to a selectivity of nearly 7 at 80° C. (176° F.).

Figure 2:
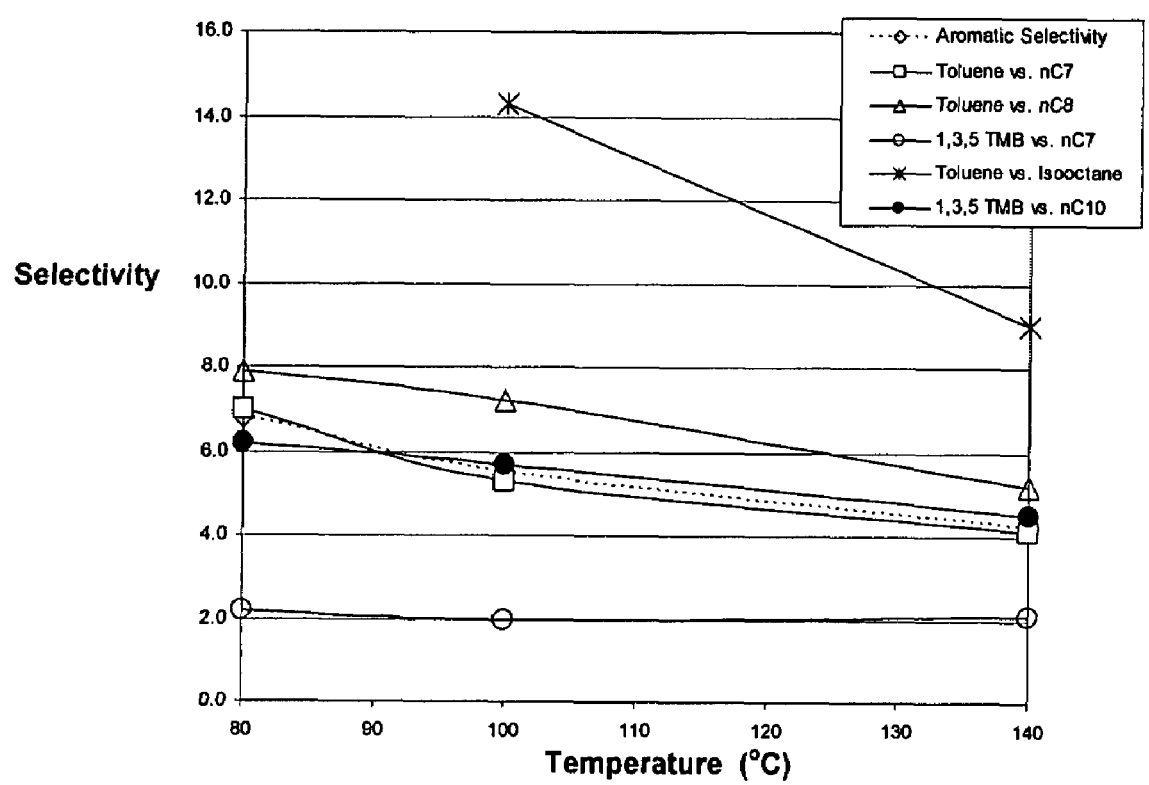
FIG. 2 shows various feedstream component separation selectivities of a membrane assembly composed of one embodiment of the membranes of the present invention subjected to a model gasoline feed under pervaporation conditions.
Figure 3:
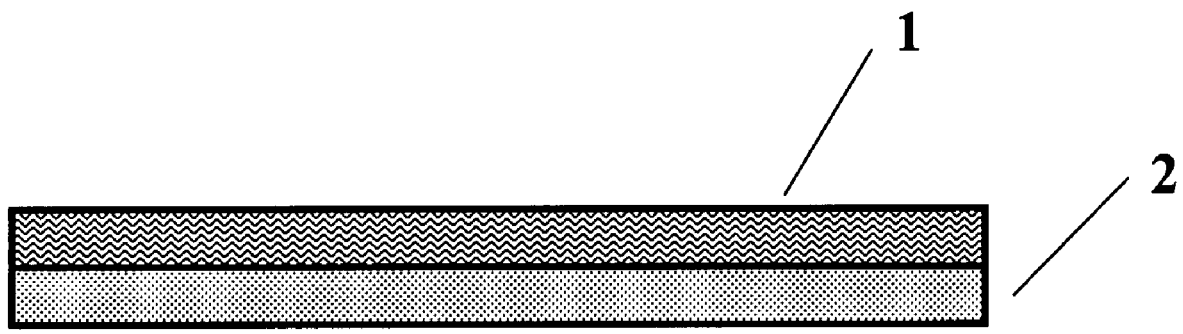
FIG. 3 illustrates one embodiment of a membrane assembly of the present invention wherein the copolymer membrane composition is cast upon a suitable support material.

FIG. 2 shows various feedstream component separation selectivities for the same membrane assembly and feed composition and pervaporation conditions as described in FIG. 1 above. As can be seen from FIG. 2, between the temperatures of 100° C. (212° F.) and 140° C. (284° F.), the membrane exhibits a very high selectivity for separating toluene from isooctane, ranging from about 9 to over 14. The membrane selectivity for the separation of toluene from normal paraffins, though somewhat lower, is also substantial at a selectivity ranging from about 4 to about 8.

In one embodiment, the present invention relates to a polymeric membrane composition wherein APD is utilized as a hard segment chain extender. In particular, the invention relates to a copolymer composition of matter comprised of a polyimide hard segment and a soft segment containing an aliphatic polyester wherein said polyimide hard segment is comprised of pyromellitic dianhydride (PMDA) and 4-aminophenyl disulfide (APD). As discussed, this membrane composition has advantages of utilizing a non-hazardous chain extender as well as possessing new and superior properties to the polymeric membrane compositions of the prior art.

The invention is not limited to the use of a polyadipate to form the membrane soft segments. Other compounds may also be utilized in the membrane compositions of the present invention including, but not limited to, a polysuccinate, a polymalonate, a polyoxalate, and a polyglutarate. Different soft segment materials may be utilized to obtain desired final separation characteristics (e.g., flux and selectivity) as well as to obtain a composition that may have unique or superior manufacturing and handling properties. It should also be noted that mixtures of different molecular weight concentrations also may be utilized in the manufacturing process to alter or improve the final process characteristics of the membrane. An example of this is shown in Table 1 where a "50/50 PEA 1000/2000" membrane was manufactured by copolymerizing a 50/50 molar ratio of two PEAs of two different molecular weights. The resultant membrane composition showed improved aromatic separation properties as can be seen in Table 1.

In another preferred embodiment, the membrane composition is comprised of a polyimide hard segment and a soft segment that are chemically cross-linked with improved glass transition temperatures ($T_g$) of the hard and soft segments of the resultant membranes. In a preferred embodiment of the present invention, the membrane has a soft segment $T_g$ of less than 77° F. (25° C.), preferably less than 32° F. (0° C.), more preferably less than –13° F. (–25° C.). In another embodiment, the membrane also has a hard segment $T_g$ of greater than 212° F. (100° C.), preferably greater than 248° F. (120° C.). All glass transition temperatures referenced herein are based measurements taken from a solvent-free membrane after fabrication and prior to exposure to any external feed or pre-treatment media (i.e., in the "unswollen" condition).

In a yet another preferred embodiment, the membrane composition of the present invention is comprised of polyethylene adipate (PEA), pyromellitic dianhydride (PMDA), 4-aminophenyl disulfide (APD), and a chemical cross-linking compound. A particularly preferred compositional embodiment, as shown in Example 1, is comprised of polyethylene adipate (PEA), pyromellitic dianhydride (PMDA), 4-aminophenyl disulfide (APD), and a chemical cross-linking agent.

In another more preferred embodiment, the polyethylene adipate (PEA) is present in a molar range of about 0.25 to about 2.0, the pyromellitic dianhydride (PMDA) is present in a molar range of about 0.5 to about 4.0, the 4-aminophenyl disulfide (APD) is present in a molar range of about 0.25 to about 2.0, and the chemical cross-linking compound is present in a molar range of about 0.5 to about 4.0. More preferably, the polyethylene adipate (PEA) is present in a molar range of about 0.5 to about 1.5, the pyromellitic dianhydride (PMDA) is present in a molar range of about 1.0 to about 3.0, the 4-aminophenyl disulfide (APD) is present in a molar range of about 0.5 to about 1.5, and the chemical cross-linking compound is present in a molar range of about 1.0 to about 3.0. Even more preferably, the polyethylene adipate (PEA), the pyromellitic dianhydride (PMDA), the 4-aminophenyl disulfide (APD), and chemical cross-linking agent are present in molar amounts of substantially 1, 2, 1, and 2, respectively.

In another preferred embodiment, the chemical cross-linking agent is selected from diepoxycyclooctane, diepoxyoctane, 1,3-butadiene diepoxide, glycerol diglycidyl ether, bisphenol A diglycidyl ether, 1,4-butanediol diglycidyl ether, 1,4-cyclohexanedimethanol diglycidyl ether, bisphenol F diglycidyl ether, neopentyl glycol diglycidyl ether, and poly (propylene glycol)diglycidyl ether. Preferably, the chemical cross-linking agent is selected from diepoxycyclooctane, diepoxyoctane, and 1,3-butadiene diepoxide.

The membrane compositions and configurations of the present invention can also be utilized in both unsupported and supported configurations. A non-limiting example of an unsupported membrane configuration includes casting the membrane on a glass plate and subsequently removing it after the chemical cross-linking reaction is completed. Non-limiting examples of supported membrane configurations include casting the membrane onto a support material fabricated from materials such as, but not limited to, polytetrafluoroethylene (e.g., Teflon®), aromatic polyamide fibers (e.g., Nomex® and Kevlar®), porous metals, sintered metals, porous ceramics, polyesters, polyamides (i.e., nylons), activated carbon fibers, latex, silicone, permeable (porous) polymers including polyvinylfluoride, polyvinylidenefluoride, polyurethanes, polypropylenes, polyethylenes, polycarbonates, polysulfones, and polyphenylene oxides, metal and polymer foams (open-cell and closed-cell foams), silica, porous glass, mesh screens, and combinations thereof. Preferably, the polymeric membrane support is selected from polytetrafluoroethylene, aromatic polyamide fibers, porous metals, sintered metals, porous ceramics, polyesters, polyamides (i.e., nylons), activated carbon fibers, latex, silicone, permeable (porous) polymers including polyvinylfluoride, polyvinylidenefluoride, polyurethanes, polypropylenes, polyethylenes, polycarbonates, polysulfones, and polyphenylene oxides and combinations thereof.

The membrane compositions and configurations of the present invention can be employed in separation processes that employ a membrane in any workable housing configuration such as, but not limited to, flat plate elements, wafer elements, spiral-wound elements, porous monoliths, porous tubes, or hollow fiber elements.

Alternative preferred embodiments for support configurations, support compositions, and methods for incorporating the membrane compositions described herein onto supports are more fully described in a concurrently filed, co-pending U.S. Patent Application Ser. No. 60/836,319 filed on Aug. 8, 2006 entitled "Polymer-Coated Inorganic Membrane for Separating Aromatic and Aliphatic Compounds" which is herein incorporated by reference.

FIG. 2 is an illustration of a preferred embodiment of a supported membrane assembly of the present invention wherein the membrane copolymer compound of the present invention (1) is incorporated onto a suitable support material (2). Suitable membrane copolymer compounds and support materials can be selected from those described herein.

In another embodiment, the present invention relates to a method of making a polymeric membrane of the present invention comprised of a) combining polyethylene adipate (PEA) diol with pyromellitic dianhydride (PMDA), then b) adding 4-aminophenyl disulfide (APD), then c) adding a chemically cross-linking compound. Preferably, the polyethylene adipate (PEA) is present in a molar range of about 0.25 to about 2.0, the pyromellitic dianhydride (PMDA) is present in a molar range of about 0.5 to about 4.0, the 4-aminophenyl disulfide (APD) is present in a molar range of about 0.25 to about 2.0, and the chemically cross-linking compound is present in a molar range of about 0.5 to about 4.0. More preferably, the polyethylene adipate (PEA) is present in a molar range of about 0.5 to about 1.5, the pyromellitic dianhydride (PMDA) is present in a molar range of about 1.0 to about 3.0, the 4-aminophenyl disulfide (APD) is present in a molar range of about 0.5 to about 1.5, and the chemically cross-linking compound is present in a molar range of about 1.0 to about 3.0. Even more preferably, the polyethylene adipate (PEA), the pyromellitic dianhydride (PMDA), the 4-aminophenyl disulfide (APD), and chemically cross-linking compound are present in molar amounts of substantially 1, 2, 1, and 2, respectively.

The membranes described herein are useful for separating a selected component or species from a liquid feed, a vapor/liquid feed, or a condensing vapor feeds. The resultant membranes of this invention can be utilized in both perstractive and pervaporative separation processes.

In a preferred embodiment, the permeate is removed from the permeate zone by a liquid or vapor sweep stream. The permeate dissolves into the sweep stream and is conducted away by sweep stream flow in order to prevent the accumulation of permeate in the permeate zone.

Membrane separation will preferentially operate at a temperature less than the temperature at which the membrane performance would deteriorate or the membrane would be physically damaged or decomposed. For hydrocarbon separations, the membrane temperature would preferably range from about 32° F. to about 950° F. (0 to 510° C.), and more preferably from about 75° F. to about 500° F. (24 to 260° C.).

In a still another preferred embodiment, the operating pressure range in the retentate zone is from about atmospheric pressure to about 150 psig. The operating pressure ranges in the permeate zone is from about atmospheric pressure to about 1.0 mm Hg absolute.

The membranes of this invention are useful for separating a desired species or component from a feedstream, preferably a hydrocarbon feedstream.

In a preferred embodiment, the membrane compositions and configurations above are utilized for the selective separation of aromatics from a hydrocarbon feedstream containing aromatics and non-aromatics.

In another embodiment, the membrane compositions and configurations above are utilized to selectively separate sulfur and nitrogen heteroatoms from a hydrocarbon stream containing sulfur heteroatoms and nitrogen heteroatoms.

In still another embodiment, the hydrocarbon feedstream is a naphtha with a boiling range of about 80 to about 450° F. (27 to 232° C.), and contains aromatic and non-aromatic hydrocarbons. In a preferred embodiment, the aromatic hydrocarbons are separated from the naphtha feedstream. As used herein, the term naphtha includes thermally cracked naphtha, catalytically cracked naphtha, and straight-run naphtha. Naphtha obtained from fluid catalytic cracking processes ("FCC") are particularly preferred due to their high aromatic content.

Although the present invention has been described in terms of specific embodiments, it is not so limited. Suitable alterations and modifications for operation under specific conditions will be apparent to those skilled in the art. It is therefore intended that the following claims be interpreted as covering all such alterations and modifications as fall within the true spirit and scope of the invention.

EXAMPLES

Example 1

Synthesis of a PEA Soft Segment and APD/PMDA Hard Segment Diepoxide Cross-Linked Copolymer Membrane, "PEI-DECO(APD)(PEA 1000)"

In the synthesis, 5 g (0.005 moles) of polyethylene adipate (PEA) diol (1000 g/mole) was reacted with 2.18 g (0.01 moles) of pyromellitic dianhydride (PMDA) to make a prepolymer in the end-capping step (165° C. for 6.5 hours). To this solution was added 45 g of dimethylformamide (DMF). The temperature was allowed to decrease to 70° C. 1.24 g (0.005 moles) of 4-aminophenyl disulfide (APD) was subsequently added (dissolved in 5 g DMF). In the DMF solution, one mole of the prepolymer reacts with one mole of APD to make a copolymer containing polyamic acid hard segment and PEA soft segment in the chain-extension step. An additional 50 g of DMF was then added. Subsequently, 100 g acetone was added to prevent gelling. The resulting solution was then stirred for 1.5 hours at 70° C. The solution was then cooled to room temperature under continual stirring conditions. Diepoxycyclooctane (1.4 g) was added to the copolymer-DMF solution at a diepoxide/PEA molar ratio of 2.

The final solution was cast onto a porous support of 0.2 micron porous Goretex® Teflon® and the thickness was adjusted by means of a casting knife. The membrane casting was first dried at a suitable temperature (e.g., room temperature) to remove most of the solvent (i.e., solvent evaporation), and subsequently low-temperature cured to promote chemical crosslinking at 150° C. (302° F.) for 1.5 hours to promote the reaction of diepoxide with pendent carboxylic acid groups. In the initial drying step, DMF and acetone were evaporated from the membrane in a box purged with nitrogen gas at room temperature for approximately 12 hours. The final curing step converts the polyamide ester hard segment to the polyimide hard segment via the imide ring closure. The final thickness of the membrane polymer coating was 10 microns.

In the synthesis with PEA, PMDA, APD and diepoxide at a molar ratio of 1/2/1/2, the chemical crosslinking reaction occurs among pendent carboxylic acid groups adjacent to the ester linkages located between polyimide hard segments and polyester soft segments. The degree of chemical crosslinking can be varied by controlling the concentration of diepoxide incorporated into the multiblock structure.

Example 2

Synthesis of a PEA Soft Segment MOCA/PMDA Hard Segment Diepoxide Cross-Linked Copolymer Membrane, "PEI-DECO(MOCA)(PEA 2000)", and PEA Soft Segment APD/PMDA Hard Segment Diepoxide Cross-Linked Copolymer Membranes, "PEI-DECO(APD)(PEA 1000)" and "PEI-DECO (APD) (50/50 PEA 1000/2000)"

The "PEI-DECO(MOCA)(PEA 2000)", "PEI-DECO (APD)(PEA 1000)" and "PEI-DECO(APD) (50/50 PEA 1000/2000)" comparative membranes illustrated in Table 1 were fabricated with similar techniques as the "PEI-DECO (APD) (PEA 1000)" membrane detailed in Example 1. Modifications in the stoichiometry of the soft segment compositions (i.e. 50/50 molar ratio), molecular weight changes in the soft segments (i.e., 2000 g/mol) and molar ratios are performed via methodologies well known in the art.

Example 3

Comparative Data of the APD/PMDA Hard Segment Copolymer Membrane Vs. the MOCA/PMDA Hard Segment Copolymer Membrane Two 10 micron disc coupons of 4.7652 cm (1⅞") diameter were cut from each membrane assembly of the three APD/PMDA hard segment membranes of Examples 1 and 2. Similarly, two 10 micron disc coupons of 4.7652 cm (1⅞") diameter were cut from the membrane assembly of the MOCA/PMDA hard segment membrane of Example 2. In each case, the two 10 micron discs were placed face to face on a very fine flat stainless steel screen and sealed in a membrane holder with a teflon o-ring. The membrane holders were maintained at the desired temperature in a thermostated oven. The effective area each of the membrane assemblies was 9.5 cm² (1.47 in²).

The membrane coupons were evaluated using a model gasoline feed having the following nominal composition (by wt): 10% 2,2,4-trimethylpentane (isooctane), 40% n-heptane, 20% toluene, 10% n-octane, 10% mesitylene, and 10% n-decane. The feed was preheated to the desired temperature and flowed over the membrane at 3.6 l/hr (0.951 gal/hr). Inlet pressure was held at 262 kPag (38.0 psig) and oven temperatures ranged from 80 to 140° C. (176 to 284° F.). A vacuum of 2 mmHg was maintained on the opposing (screen) side of the membrane. Permeate was collected under vacuum using traps in series cooled with dry ice and liquid nitrogen respectively. Typical permeation rates of less than 2 g/hr (0.0044 lb/hr) were observed, corresponding to less than 0.06% permeate on feed. In effect, differential yields on feed.

Table 1 shows the results of using these membranes in separating the aromatic and aliphatic components of a regular gasoline. It should be noted that 50/50 PEA 1000/2000 implies that a 50/50 molar ratio of two PEAs of two different molecular weights were copolymerized. PEA 1000 and PEA 2000 designates 1000 g/mole and 2000 g/mole, respectively.

TABLE 1

| Membrane Assembly Designation | Flux (g/s-m²) | Aromatic Selectivity | Selectivity of Toluene vs. $nC_7$ | Selectivity of Toluene vs. Isooctane | Selectivity of Toluene vs. $nC_8$ |
|---|---|---|---|---|---|
| PEI-DECO (MOCA) (PEA 2000) | 0.17 | 5.33 | 5.29 | 11.97 | 7.12 |
| PEI-DECO (APD) (PEA 2000) | 0.29 | 4.16 | 4.05 | 8.03 | 5.25 |
| PEI-DECO (APD) (50/50 PEA 1000/2000) | 0.06 | 5.83 | 5.81 | 15.47 | 6.92 |
| PEI-DECO (APD) (PEA 1000) | 0.04 | 5.47 | 5.39 | 14.28 | 7.20 |

As can be seen from the data in the first two rows of Table 1, the use of APD as a chain extender resulted in a flux increase of 70% (0.29 g/s-m² vs. 0.17 g/s-m²) over the membranes of the prior art which utilized MOCA as a chain extender with only an associated 22% decrease in aromatic selectivity (4.16 vs. 5.33). The three associated component comparisons (toluene vs. $nC_7$, toluene vs. isooctane, and toluene vs. $nC_8$) all follow similar selectivities.

It can also be seen from the last two rows in Table 1 that the selectivity of the PEI-DECO (APD) membrane can be increased by adjusting the molecular weight and molecular weight compositions of the PEA utilized in the membrane composition.

What is claimed is:

1. A copolymer membrane, comprising a polyimide membrane hard segment and an aliphatic polyester membrane soft segment, wherein said polyimide membrane hard segment is comprised of a dianhydride and 4-aminophenyl disulfide (APD).

2. The copolymer membrane of claim 1, wherein the membrane soft segment is comprised of a compound selected from the group consisting of a polyadipate, a polysuccinate, a polymalonate, a polyoxalate, and a polyglutarate.

3. The copolymer membrane of claim 1, wherein the glass transition temperature, $T_g$, of the membrane soft segment is less than 77° F. (25° C.).

4. The copolymer membrane of claim 3, wherein the copolymer membrane composition is comprised of a polyadipate, a dianhydride, 4-aminophenyl disulfide (APD), and a cross-linking agent.

5. The copolymer membrane of claim 4, wherein the cross-linking agent is selected from diepoxycyclooctane, diepoxyoctane, 1,3-butadiene diepoxide, glycerol diglycidyl ether, bisphenol A diglycidyl ether, 1,4-butanediol diglycidyl ether, 1,4-cyclohexanedimethanol diglycidyl ether, bisphenol F diglycidyl ether, neopentyl glycol diglycidyl ether, and poly (propylene glycol)diglycidyl ether.

6. The copolymer membrane of claim 5, wherein the polyadipate, the dianhydride, 4-aminophenyl disulfide (APD), and the cross-linking agent are present in molar ratios of about 0.25 to about 2.0, about 0.5 to about 4.0, about 0.25 to about 2.0, and about 0.5 to about 4.0, respectively.

7. The copolymer membrane of claim 6, wherein the glass transition temperature, $T_g$, of the membrane soft segment is less than 32° F. (0° C.) and wherein the glass transition temperature, $T_g$, of the membrane hard segment is greater than 248° F. (120° C.).

8. The copolymer membrane of claim 7, wherein the polyadipate is comprised of a polyethylene adipate and the dianhydride is comprised of a pyromellitic dianhydride.

9. A method for making a polymeric membrane, comprising:
   a) reacting a polyadipate with a dianhydride to form a prepolymer;
   b) adding 4-aminophenyl disulfide (APD) to the prepolymer to form a first solution;
   c) adding a cross-linking agent to the first solution to form a second solution;
   d) incorporating the second solution onto a suitable support; and
   e) curing the second solution at a temperature of from about 212° F. to about 482° F. (100 to 250° C.).

10. The method for making the polymeric membrane of claim 9, wherein the polyadipate, the dianhydride, 4-aminophenyl disulfide (APD), and the cross-linking agent are present in molar ratios of about 0.25 to about 2.0, about 0.5 to about 4.0, about 0.25 to about 2.0, and about 0.5 to about 4.0, respectively.

11. The method for making the polymeric membrane of claim 10, comprising a curing duration of at least 0.5 hours.

12. The method for making the polymeric membrane of claim 10, wherein the polyadipate is comprised of polyethylene adipate, the dianhydride is comprised of pyromellitic dianhydride, and the cross-linking agent is selected from diepoxycyclooctane, diepoxyoctane, and 1,3-butadiene diepoxide.

13. The method for making a polymeric membrane of claim 12, wherein the first solution is maintained at a temperature of less than about 80° F. (27° C.) for at least 24 hours prior to incorporation of the cross-linking agent.

14. The method for making the polymeric membrane of claim 13, wherein the second solution is cured at a temperature of from about 212° F. to about 392° F. (100 to 200° C.).

15. A process for selectively separating a desired component from a hydrocarbon feedstream, comprising:
   a) contacting the hydrocarbon feedstream with one side of a polymeric membrane assembly comprised of a housing containing at least one membrane element and at least one support material, wherein the membrane element is comprised of a polyimide hard segment and a soft segment, the polyimide hard segment is comprised of a dianhydride and 4-aminophenyl disulfide (APD), and the glass transition temperature, $T_g$, of the soft segment of the membrane element is less than 77° F. (25° C.), and
   b) retrieving a permeate from the opposite side of the polymeric membrane assembly; wherein the concentration by wt % of the desired component in the permeate stream is higher than the concentration by wt % of the desired component in the hydrocarbon feedstream.

16. The process of claim 15, wherein the desired component is an aromatic compound.

17. The process of claim 15, wherein the desired component is a sulfur heteroatom.

18. The process of claim 15, wherein the desired component is a nitrogen heteroatom.

19. The process of claim 16, wherein the membrane element is comprised of a cross-linking agent selected from diepoxycyclooctane, diepoxyoctane, 1,3-butadiene diepoxide, glycerol diglycidyl ether, bisphenol A diglycidyl ether, 1,4-butanediol diglycidyl ether, 1,4-cyclohexanedimethanol diglycidyl ether, bisphenol F diglycidyl ether, neopentyl glycol diglycidyl ether, and poly(propylene glycol)diglycidyl ether.

20. The process of claim 19, wherein the hydrocarbon feedstream is comprised of a naphtha with a boiling range of about 80 to about 450° F. (27 to 232° C.).

21. The process of claim 20, wherein the glass transition temperature, $T_g$, of the soft segment of the membrane element is less than 32° F. (0° C.) and the $T_g$ of the hard segment of the membrane element is greater than 248° F. (120° C.).

* * * * *